(12) United States Patent
Laubert et al.

(10) Patent No.: US 10,206,720 B2
(45) Date of Patent: Feb. 19, 2019

(54) FASTENER, SPINAL INTERBODY SYSTEM INCLUDING SAME AND METHOD

(71) Applicant: AESCULAP IMPLANT SYSTEMS, LLC, Center Valley, PA (US)

(72) Inventors: Nikolay Laubert, Center Valley, PA (US); James W. Adams, Center Valley, PA (US); John Nixon, Center Valley, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 579 days.

(21) Appl. No.: 14/476,529

(22) Filed: Sep. 3, 2014

(65) Prior Publication Data

US 2016/0058480 A1  Mar. 3, 2016

(51) Int. Cl.
*A61B 17/84* (2006.01)
*A61B 17/80* (2006.01)
(Continued)

(52) U.S. Cl.
CPC ........ *A61B 17/7059* (2013.01); *A61B 17/808* (2013.01); *A61B 17/8052* (2013.01);
(Continued)

(58) Field of Classification Search
CPC . A61B 17/808; A61B 17/844; A61B 17/8605; A61B 17/8615; A61B 17/8625; A61B 17/8645; A61B 17/8685; A61B 17/8033; A61B 17/8052; A61B 2017/8655; A61F 2/4455; A61F 2/447
See application file for complete search history.

(56) References Cited

U.S. PATENT DOCUMENTS 5,531,554 A * 7/1996 Jeanson ............. A61B 17/8605
411/107
5,931,838 A 8/1999 Vito
(Continued)

FOREIGN PATENT DOCUMENTS

EP       2 018 827 A1   1/2009
WO   2013175147 A1   11/2013

OTHER PUBLICATIONS

Extended European search report for the related European Patent Application No. 15181356.5 dated Feb. 2, 2016.

*Primary Examiner* — Matthew J Lawson
*Assistant Examiner* — Amy R Sipp
(74) *Attorney, Agent, or Firm* — Kenealy Vaidya LLP

(57) ABSTRACT

The disclosed subject matter includes a fastener, a system and methods for use and manufacture. The fastener can include a head disposed at a proximal end of the fastener, a shaft connected to the head, and at least one of the head and the shaft can include a plurality of flat surfaces. A collar can extend about the longitudinal axis of the fastener and can have a proximal-most surface spaced in a longitudinal axis direction away from a proximal-most surface of the fastener. The collar can include a plurality of petals spaced about the longitudinal axis, each of the plurality of petals including a flat surface facing a respective one of the plurality of flat surfaces of the at least one of the head and the shaft. A plate and/or a cage can be included with the fastener for use in a spinal connection, kit or repair system.

20 Claims, 11 Drawing Sheets

(51) Int. Cl.
  *A61B 17/70* (2006.01)
  *A61F 2/44* (2006.01)
  *A61F 2/46* (2006.01)
  *A61B 17/86* (2006.01)
  *A61B 17/00* (2006.01)

(52) U.S. Cl.
  CPC ........ *A61B 17/844* (2013.01); *A61B 17/8605* (2013.01); *A61B 17/8625* (2013.01); *A61F 2/447* (2013.01); *A61F 2/4455* (2013.01); *A61F 2/4611* (2013.01); *A61B 2017/00867* (2013.01); *A61F 2002/449* (2013.01)

(56) References Cited

U.S. PATENT DOCUMENTS

| | | |
|---|---|---|
| 6,261,291 B1 | 7/2001 | Talaber et al. |
| 7,857,839 B2 | 12/2010 | Duong et al. |
| 7,963,982 B2 | 6/2011 | Kirschman |
| 8,048,131 B2 | 11/2011 | Dalton |
| RE43,008 E | 12/2011 | Talaber et al. |
| 8,298,272 B2 | 10/2012 | Edie et al. |
| 8,574,271 B2 | 11/2013 | Crainich |
| 8,753,396 B1* | 6/2014 | Hockett ............... A61F 2/442 623/17.11 |
| 9,005,293 B2 | 4/2015 | Moskowitz et al. |
| 2006/0276793 A1* | 12/2006 | Berry ............... A61B 17/8052 606/70 |
| 2008/0177330 A1 | 7/2008 | Ralph et al. |
| 2012/0078373 A1* | 3/2012 | Gamache ........... A61B 17/8625 623/17.16 |
| 2012/0303071 A1* | 11/2012 | Black ............... A61B 17/8047 606/305 |
| 2014/0114415 A1* | 4/2014 | Tyber ................ A61F 2/4455 623/17.16 |

* cited by examiner

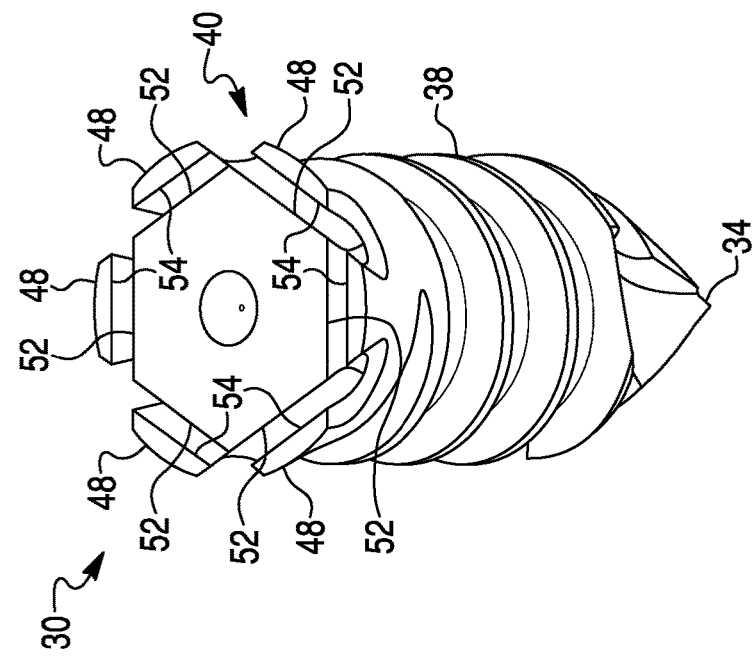
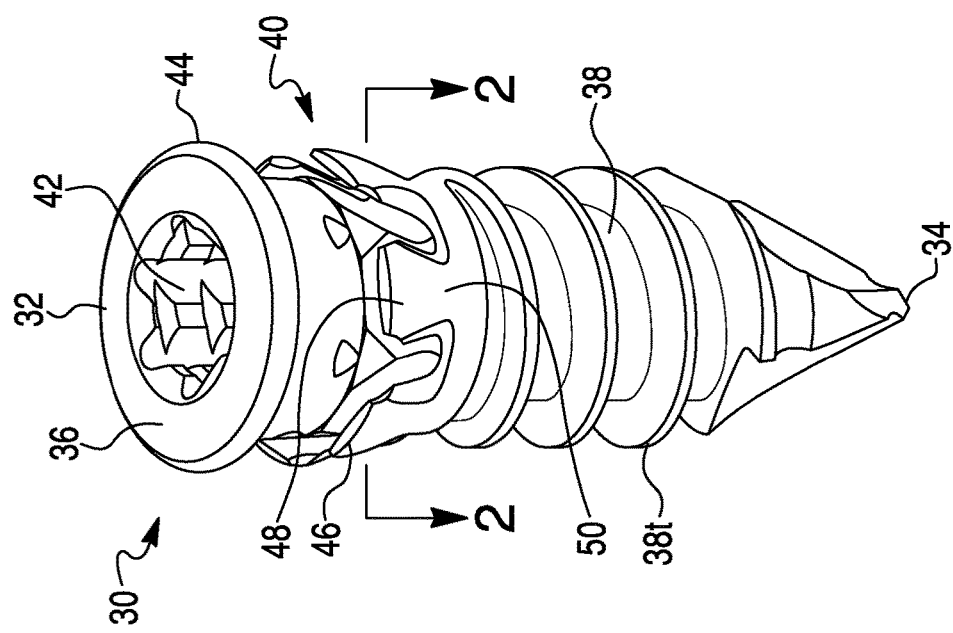

FASTENER, SPINAL INTERBODY SYSTEM INCLUDING SAME AND METHOD

BACKGROUND

1. Field

The presently disclosed subject matter relates generally to fasteners. In particular, the disclosed subject matter relates to surgical fasteners and methods for use in implanting an interbody device between adjacent or separate (i.e. neighboring but not necessarily naturally adjacent) vertebrae.

2. Background

Fasteners have commonly been used in surgical applications for attaching tissue, such as bone, to various other structures, such as medical devices or implants, other bone structure, soft tissue such as muscle or ligaments, etc.

In one application, in order to stabilize two adjacent or separate vertebrae of the spine, medical professionals will typically place a first component, commonly referred to as a cage, between adjacent target vertebrae. The cage will then be secured to the vertebrae using bone screws that traverse angled apertures in the cage to attach to upper and lower target vertebrae. Sometimes, a second component, typically referred to as a plate, is attached to both the cage and the upper and lower target vertebrae via fastener(s). The plate acts to further secure the cage in position and prevents back-out and/or movement or migration of the cage itself. One example of such a plate used with a cage device and which includes fasteners for securing the plate to a patient's vertebrae is disclosed in the present Applicant's U.S. patent application Ser. No. 13/944,545 entitled "Spinal Interbody Device, System and Method," the disclosure of which is incorporated herein by reference.

Fasteners currently available are not typically designed for use with the above-referenced cage and plate structures. In addition, further fastening devices and/or materials are sometimes needed to ensure proper adherence and tolerances are maintained between the plate and certain fasteners.

SUMMARY

Accordingly, it may be beneficial to provide a fastener or fastener and plate/cage system and related methods that includes features that allow a practitioner to quickly and easily lock the plate device to a patient, to ensure or maintain both adherence and spacing between structures, and which would also include a minimal number of parts or materials for manufacture.

According to one aspect of the disclosure, a fastener can have a proximal end, a distal end, and a longitudinal axis extending from the proximal end to the distal end. The fastener can include a head disposed at the proximal end of the fastener, and a shaft connected to the head and extending to the distal end of the fastener. At least one of the head and the shaft can include a plurality of flat surfaces. A collar can extend about the longitudinal axis and have a proximal-most surface spaced in a longitudinal axis direction away from a proximal-most surface of the fastener, with the collar including a plurality of petals spaced about the longitudinal axis. Each of the plurality of petals can include a flat surface facing a respective one of the plurality of flat surfaces of the at least one of the head and the shaft.

According to another aspect of the disclosed subject matter, a fastener can include a first end, a second end, and a longitudinal axis extending from the first end to the second end. The fastener can include a head disposed at the first end of the fastener, a shaft connected to the head and extending to the second end of the fastener, with at least one of the head and the shaft including a plurality of flat surfaces. A collar can extend about the longitudinal axis, with the collar being spaced in its entirety from a proximal most surface of the first end of the fastener in a longitudinal axis direction. The collar can include a plurality of petals spaced about the longitudinal axis.

According to another aspect of the disclosed subject matter, a fastener can include a first end, a second end, and a longitudinal axis extending from the first end to the second end. The fastener can include a head disposed at the first end of the fastener, a shaft connected to the head and extending to the second end of the fastener, at least one of the head and the shaft including a plurality of flat surfaces. A collar can extend about the longitudinal axis and be spaced in a longitudinal axis direction from the first end of the fastener, the collar can include a plurality of petals spaced about the longitudinal axis. Each of the plurality of petals can include a root and a free end, the root being connected to the at least one of the head and the shaft, the free end being spaced from the at least one of the head and the shaft, and each of plurality of petals being thinner at the free end than at the root.

According to yet another aspect of the disclosed subject matter, a method for manufacturing a screw can include forming a head, a shaft, and a collar intermediate the head and the shaft, and cutting a plurality of peripheral slots in the collar to define a plurality of petals spaced about the longitudinal axis.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 1 is a perspective view of a fastener made in accordance with principles of the disclosed subject matter.

FIG. 2 is a cross-sectional view taken along line 2-2 of FIG. 1.

DETAILED DESCRIPTION OF EXEMPLARY EMBODIMENTS

FIG. 1 is a perspective view of an exemplary fastener 30 made in accordance with principles of the disclosed subject matter. The fastener 30 can be used alone or with additional fasteners and/or with other structure(s) to attach a first structure to a mounting structure. In particular, fastener 30 is particularly adapted for attaching a plate and cage system to a patient's vertebrae.

Figure 5:
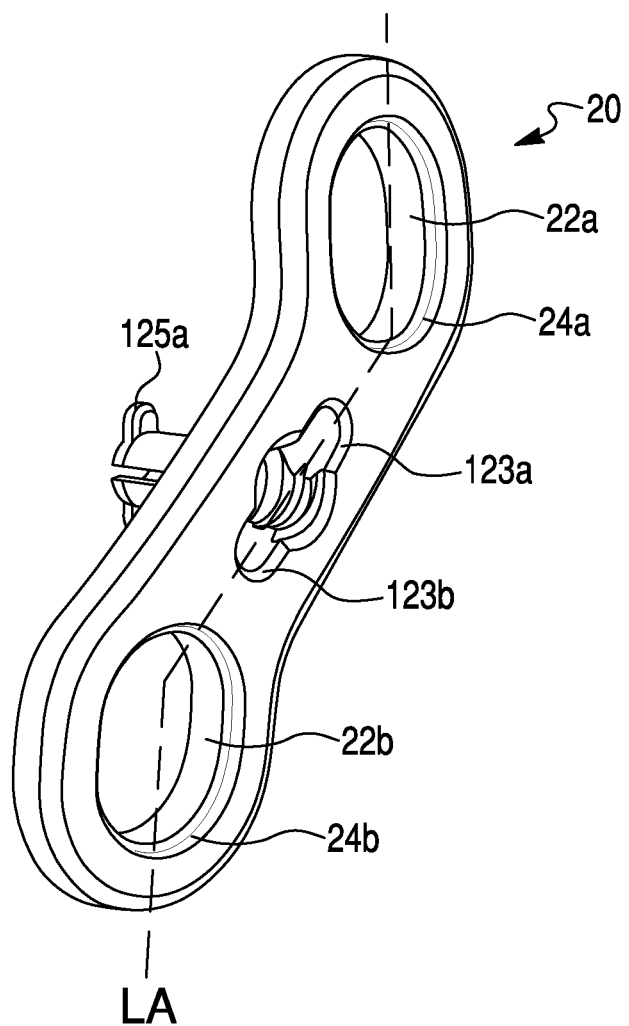
FIG. 5 is a front perspective view of the plate of the mounting system of FIG. 3.

Referring to FIGS. 1 and 5, the fastener 30 can include a first (or proximal) end 32, a second (or distal) end 34, a longitudinal axis L, a head 36, a shaft 38, and a collar 40. The longitudinal axis L can extend from the first end 32 to the second end 34. The head 36 can be disposed at the first end 32 of the fastener 30 and can have a proximal-most surface facing away from the shaft 38 of the fastener 30. The proximal-most surface of the head 36 serves as the proximal-most surface of the entire fastener 30. The shaft 38 can be connected to the head 36 and can extend to the second end 34 of the fastener 30. The collar 40 can extend radially about the longitudinal axis L and can be spaced in a longitudinal axis direction from the first end 32 of the fastener 30. In one embodiment, the collar 40 can be conical in general shape or outline, and can have a proximal-most surface or surfaces that are spaced in a longitudinal axis direction from the proximal-most surface of the head 36. Thus, as can be seen in FIG. 1, there is a first portion of the head 36 that is not enveloped by the collar 40 and a second portion of the head 36 that is enveloped at least in part by the collar 40 as viewed from a position normal to the longitudinal axis L of the fastener 30.

The head 36 can include a tool engagement structure 42 and a lip 44. The tool engagement structure 42 can be configured to mate with a tool in order to drive the fastener 30 into and/or out of the mounting structure. The tool engagement structure 42 can extend from the first end 32 of the fastener 30 towards the second end 34 of the fastener 30. The lip 44 can extend about the periphery of the head 36. The lip 44 can be greater in size than the remainder of the head 36. In an exemplary embodiment, the head 36 can be circular in a cross section taken perpendicular to the longitudinal axis, the lip 44 can extend about the circumference of the head 36, and the diameter of the lip 44 can be greater than the diameter of the remainder of the head 36.

Figure 6:
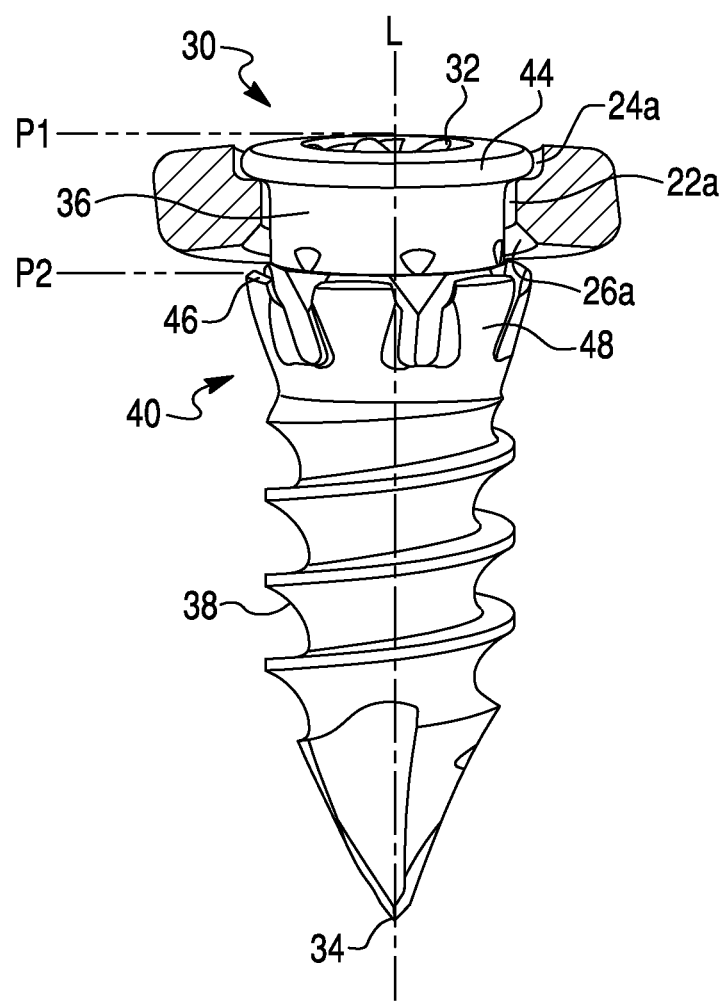
FIG. 6 is a partial cross-sectional view taken along line 6-6 of FIG. 3.

The collar 40 can extend radially about the longitudinal axis L of the fastener 30. As indicated above, the collar 40 can be spaced in a longitudinal axis direction from the first end 32 of the fastener 30 such that a "non-collared" portion of the head 36 is exposed along the longitudinal axis from a top of the collar 40 to the first end 32 of the fastener 30. The collar 40 can include a top chamfered edge 46 and can taper from the edge 46 toward the longitudinal axis L. As shown in FIG. 6, a first plane (schematically represented by line P1) that contains a proximal-most portion of the first end 32 of the fastener 30 and is perpendicular to the longitudinal axis L can be spaced from a second plane (schematically represented by line P2) that contains the top edge 46 of the conical collar 40 (a proximal-most portion of the collar 40) and is also perpendicular to the longitudinal axis L.

The collar 40 can include a plurality of petals 48 spaced radially about the longitudinal axis L. In an exemplary embodiment, the collar 40 can include six petals 48 equally spaced about the longitudinal axis. Each petal 48 can include a root 50 and a free end located at chamfered edge 46. The root 50 can be connected to the shaft 38. The free end can include the top edge 46 of the collar 40, and can face in a direction towards the first end 32. Referring to FIGS. 1, 2 and 5, the free end of each petal 48 can have a cross-sectional thickness that is less than a cross-sectional thickness measured at the root 50.

The top edge 46 of the collar 40 can be spaced apart from at least one of the head 36 and the shaft 38. Each petal 48 can be cantilevered to at least one of the head 36 and the shaft 38. In an exemplary embodiment, the top edge 46 can be spaced from the head 36 and each petal 48 can be cantilevered to the shaft 38 by the root 50. In another exemplary embodiment, the top edge 46 can be spaced from a first portion of the shaft 38 and each petal 48 can be cantilevered to a second portion of the shaft 38. In yet another exemplary embodiment, the top edge 46 can be spaced from a first portion of the head 36 and each petal 48 can be cantilevered to a second portion of the head 36. Any of these configurations can permit each petal 48 to flex relative to the shaft 38 and/or the head 36.

Referring to FIGS. 1 and 2, at least one of the head 36 and the shaft 38 can include a plurality of flat surfaces 52. The flat surfaces 52 can be radially spaced about the longitudinal axis L of the fastener 30. In an exemplary embodiment, the head 36 and/or the shaft 38 can include six flat surfaces 52 evenly distributed about the longitudinal axis L, where each flat surface 52 abuts two adjacent flat surfaces 52 such that an area bound by the flat surfaces 52 forms a hexagon when viewed in cross section along the longitudinal axis L. In other words, a cross-section of the fastener 30 taken perpendicular the longitudinal axis L will reveal a hexagon shaped area bound by the flat surfaces 52 in the presently described embodiment. Each petal 48 can include a flat surface 54 that faces a respective one of the plurality of flat surfaces 52 on the at least one of the head 36 and the shaft 38. Thus, the hexagonal shaped area defined by surfaces 52 appears to be outlined or surrounded by six slots that are each bordered by both a flat surface 52 and a respective flat surface 54 of each petal 48. These slots create openings/spacings located at apexes of the hexagon and in between each of the petals 48. In particular, the six slots can be seen when a cross-section of the fastener 30 at a location of collar 40 is viewed along the longitudinal axis of the fastener 30 (see, for example, FIG. 2).

Each of the plurality of petals 48 can be spaced about the longitudinal axis in equal or non-equal radial distances. Furthermore, the free end of each petal 48 can be spaced from the at least one of the head 36 and the shaft 38 such that an interior slot space is created between the free end of each of the petals 48 and at the least one of the head 36 and the shaft 38. Thus, the free end of each petal 48 is configured to flex into the slot space if force is applied the free end in a direction towards the longitudinal axis of the fastener 30.

The slot space can be configured to extend along a substantial portion (i.e., more than half) of the length of each petal 48 as measured from the root 50 to the outermost peripheral surface of each of the petals 48 (e.g., chamfer edge 46). If an imaginary radius that extends perpendicularly from the longitudinal axis of the fastener is viewed, it would intersect at least one of the head 36 and the shaft 38, the slot space, and at least one of the plurality of petals 48 along a substantial portion of a length of the at least one of the plurality of petals 48 (the length defined from the root to the outermost peripheral surface of each of the petals 48). Each of the petals 48 can include a chamfered edge that runs from the root 50 along either side of each of the petals 48 to a location adjacent the chamfer 46 (the chamfer 46 being substantially perpendicular in orientation with respect to the pair of chamfers that run along either side of each of the petals 48 from the root 50). The chamfers can then be configured to form a U-shaped trough between each of the petals 48, with the bottom of the U-shaped troughs separating each of the roots 50.

The surfaces that define the slots or the "slot space" as noted above can include two flat surfaces that are opposed to each other (face each other). The two flat surfaces can be substantially parallel to each other, and can extend at an acute angle with respect to the longitudinal axis of the fastener 30. More specifically, each of the flat surfaces can extend upward and at an angle(s) that is/are less than 45 degrees with respect to the longitudinal axis of the fastener 30.

Figure 9:
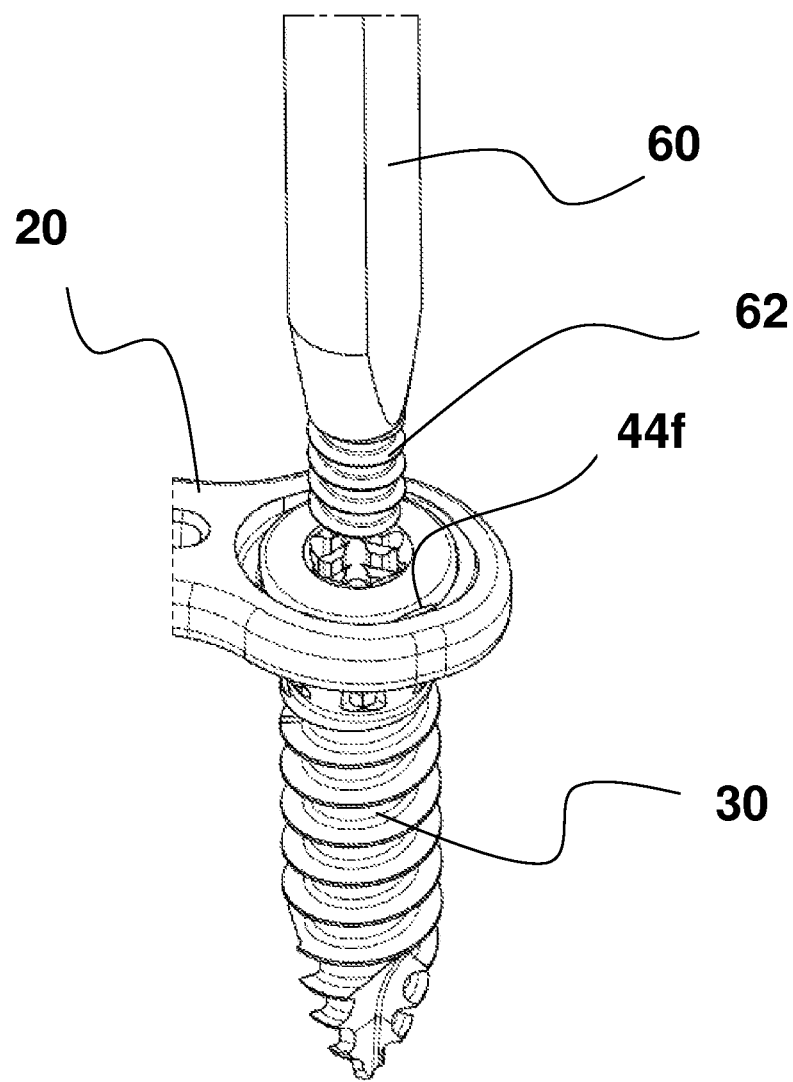
FIG. 9 is a partial perspective view of a plate, fastener, and removal tool made in accordance with principles of the disclosed subject matter.
Figures 10, 11:
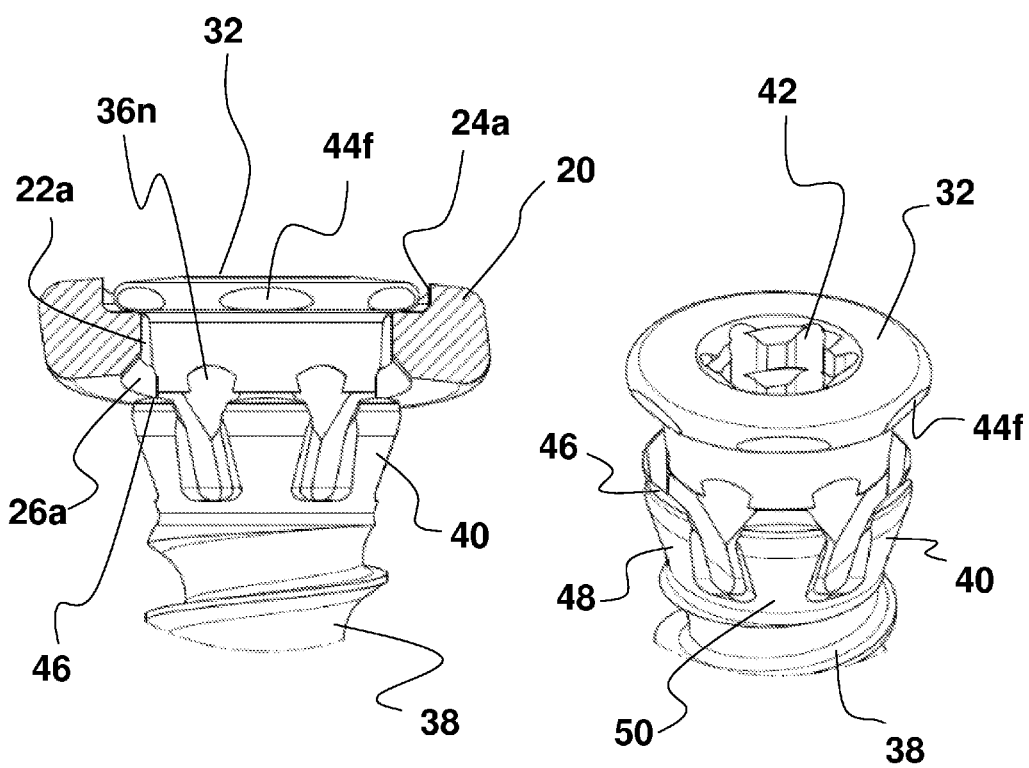
FIG. 10 is a partial lateral view of the fastener and partial cross-section view of the plate of FIG. 9.
FIG. 11 is a partial perspective view of the fastener of FIG. 9.

The collar 40, the shaft 38, and the head 36 can be integrally formed as a homogenous unit. In an exemplary embodiment, the collar 40 can be a portion of the fastener 30 that extends in an uninterrupted manner around the longitudinal axis L at a middle section of the fastener 30. The petals 48 can be formed by making a plurality of cuts into the conical collar 40 to form the flat outer surfaces 52 of the head 36 and/or the shaft 38 and the flat inner surfaces 54 of the petals 48. These cuts can also create each of the petals 48 and the space between adjacent petals 48. In addition, these cuts can create a plurality of flats 44*f* spaced about the lip 44 (as shown in FIGS. 9-11). In another embodiment, the flats 44*f* can be formed on the lip 44 prior to the creation of the petals 48 in order to act as a guide for making the cuts to form the flat surfaces 52, 54, the petals 48 and the space between each of the petals 48. Alternate methods for manufacturing the fastener are to mold the entire fastener using various injection mold techniques, blow mold techniques, casting, forming, machining, joining, printing, stereolithography, laser sintering, electrical discharge or spark erosion machining, and other known methods for manufacturing fasteners. In addition, during the manufacturing process the flats 44*f* can be made at the same time as the cuts to form the flat surfaces 52, 54.

Each of the petals 48 can be spaced from an adjacent petal 48 by a predetermined distance. The predetermined distance can be set to meet the desired performance of the petals 48 and/or to permit an advantageous method for manufacturing the fastener 30. Each petal 48 can have a cross-sectional thickness that decreases in a direction from the root 50 of the petal to the top edge 46 of the collar 40. Alternatively, the cross-sectional thickness can increase from the root 50 to the top edge of the collar 40 depending on how much flexibility/movement is desired for each petal 48 with respect to the shaft 38 or head 36 to which each petal is cantilevered.

The shape of each petal 48 can include a regular shape or an irregular shape configured to provide the desired flexing. For example, each petal 48 can have a shape such as, but not limited to, a tear drop shape, a hexagonal shape, a pentagonal shape, a rectangular shape, a triangular shape, an ovoid shape, a circular shape, a partially linear and a partially curved shape, or a polygonal shape. Depending on the shape of each petal 48, the petals can be uniformly shaped, or differently shaped with respect to each other, and can be symmetrical or non-symmetrical. In an exemplary embodiment, the petal 48 can have a hexagonal shape with at least one chamfered edge leading to the top edge 46. A chamfer can be present at each of four sides that make up the front edge 46 of the petal 48 such that the petal 48 narrows as it comes to the top edge 46.

Figure 3:
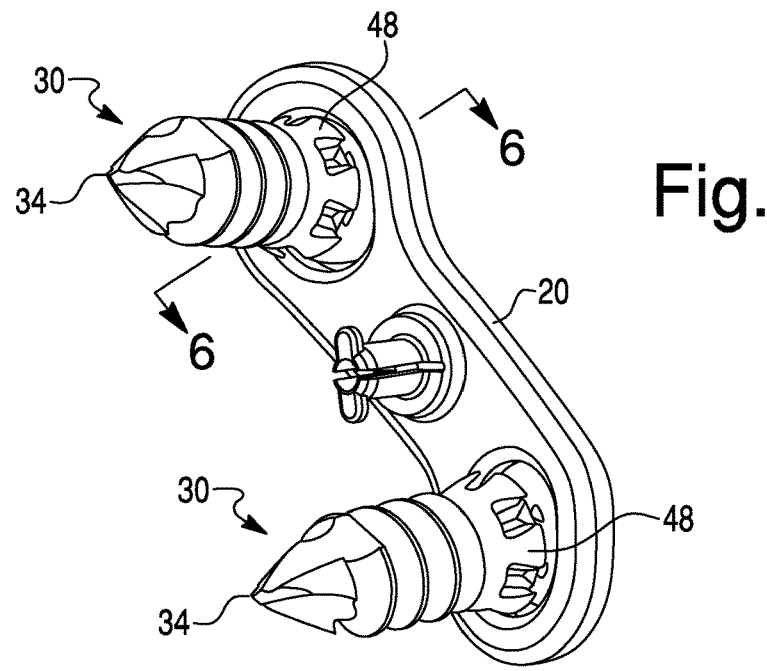
FIG. 3 is a rear perspective view of a mounting system made in accordance with principles of the disclosed subject matter.
Figure 8:
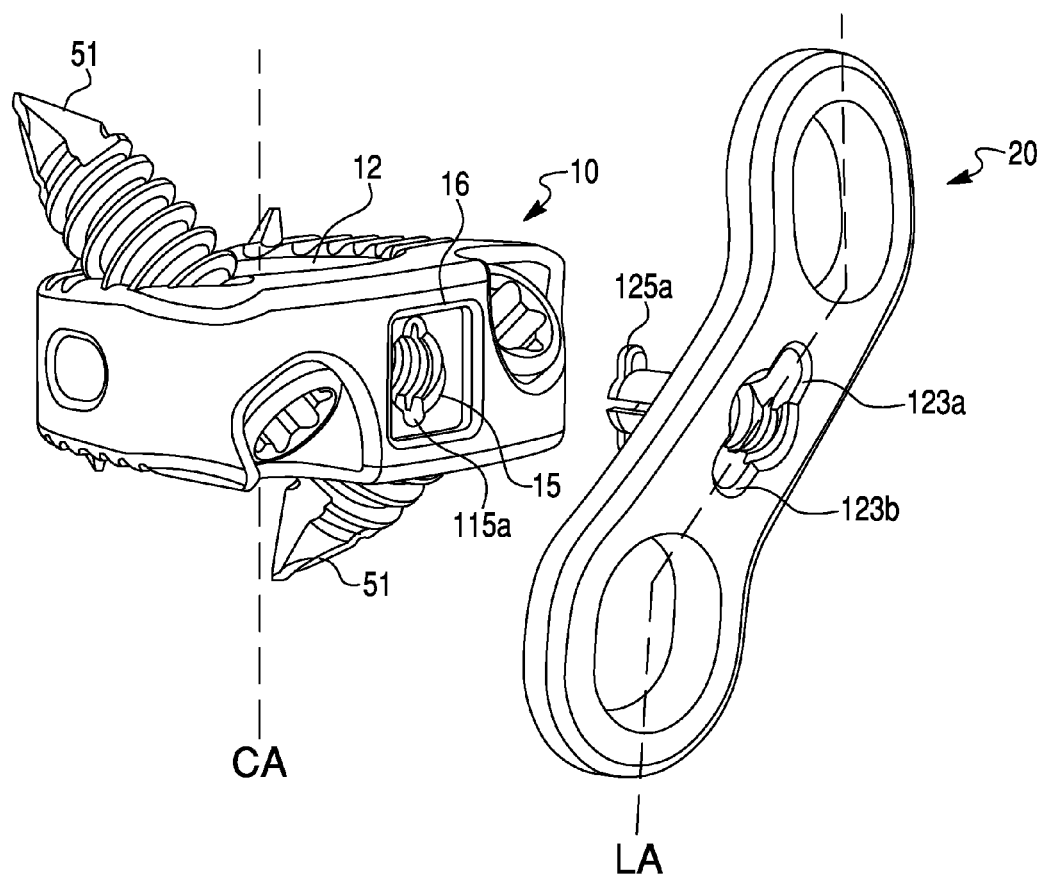
FIG. 8 is an exploded perspective anterior view of a cage and a plate of the interbody device and system of FIG. 7.

FIG. 3 is a perspective view of a mounting system that can include a plate 20 and at least one fastener 30 made in accordance with principles of the disclosed subject matter. As shown in FIGS. 3-6, the plate 20 can include at least one aperture 22*a* that can receive the fastener 30. The fastener 30 can be driven through the aperture 22*a* and into a mounting structure (e.g., a vertebrae of a patient) in order to mount the plate 20 onto the mounting structure. As shown in FIG. 8, the plate 20 can be mounted to a cage 10 which is located between vertebrae of a patient for various medical reasons. Thus, the plate 20 and fasteners 30 can provide stability and locking forces that help maintain the cage 10 in place.

The aperture 22*a* in plate 20 can be configured to cooperate with the fastener 30 to lock the fastener 30 within the aperture 22*a* if the fastener 30 is driven into a mounting structure. Any number of apertures 22*a* and corresponding number of fasteners 30 can be employed to secure the plate 20 to a mounting structure. In an exemplary embodiment, the plate 20 can include a first aperture 22*a* and a second aperture 22*b*. A respective fastener 30 can be driven through each aperture 22*a*, 22*b* in order to attach the plate 20 to a mounting structure such as vertebrae.

Figure 4:
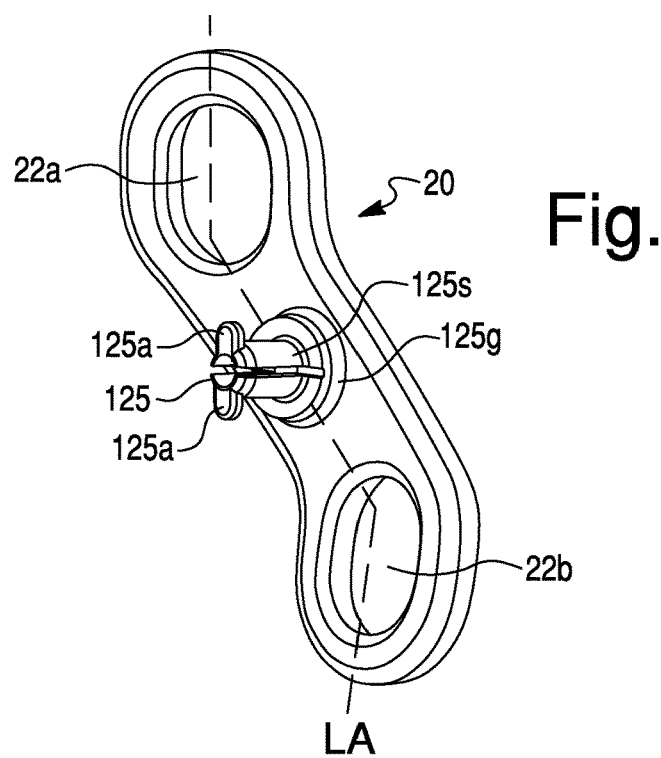
FIG. 4 is a rear perspective view of a plate of the mounting system of FIG. 3.

Referring to FIGS. 4 and 5, the plate 20 can include an annular recess or chamfer 24*a*, 24*b* that extends around each aperture 22*a*, 22*b*. In addition, as shown in FIG. 6, a chamfer 26*a*, 26*b* can extend around each aperture 22*a*, 22*b* and can be opposed to the chamfer 24*a*, 24*b* with respect to the plate 20.

FIG. 6 shows a relationship between the fastener 30 and the plate 20 after the fastener 30 has been located in (e.g., driven through) the aperture 22*a* and, in some cases, into a patient's bone, such as a vertebra, at a location below plate 20. In this view, it is clear that an outer radial most surface of the collar 40 is slightly larger than the inner circumference of aperture 22*a* of the plate 20. Thus, when the fastener 30 is located in this position, the proximal most surface of the collar 40 (in this example, top chamfered edge or surface 46) can be in contact with the inner chamfer 26*a* of the aperture 22*a*. In addition, lip 44 of head 36 can reside in and contact chamfer 24*a* on the top or proximal side of plate 20. Thus, the lip 44 and collar 40 act to sandwich the plate 20 therebetween. The force imparted by both the lip 44 and collar 40 to the plate 20 tends to keep the plate 20 in place with respect to the fastener 30, and prevents shifting of the plate 20 during use. In particular, the plurality of petals 48 that form the collar 40 can be configured such that they impart a spring force against the chamfer 26*a* after installation. The root 50 of each petal 48 can be slightly thinner (in a lateral view) than a proximal most portion (located at the top chamfered edge 46). Each petal 48 is cantilevered away from the main body of the fastener 30 and can move slightly inward and outward toward and away from a longitudinal axis of the fastener 30. Thus, the chamfered surface 26*a* of the plate 20 can cause the top chamfered edge 46 of each petal to move slightly inward towards the longitudinal axis of the fastener. The spring force of the petals 48 (which desire to move back to their original position after being moved inward by the aperture 22*a* and chamfered surface 26*a* during installation) causes the lip 44 of the fastener 30 to lock onto chamfer 24*a* located in the top portion of the aperture 22*a* of the plate 20.

When a user desires to remove the fastener 30 from the plate 20, the chamfered surface 26*a* will also assist in guiding the proximal most portion of the petals 48 further inward towards the longitudinal axis of the fastener 30 until the outermost radius of the collar 40 is narrow enough to fit back through aperture 22a in the plate 20. This removal function can be accomplished by inserting a removal tool 60 (see, for example, FIG. 9) into a top end of the fastener 30 and applying a removal force that causes the petals 48 to follow chamfer 26a and constrict such that the outermost circumference of the collar 40 is able to then fit through and be removed from the aperture 22a in the plate 20.

Figure 7:
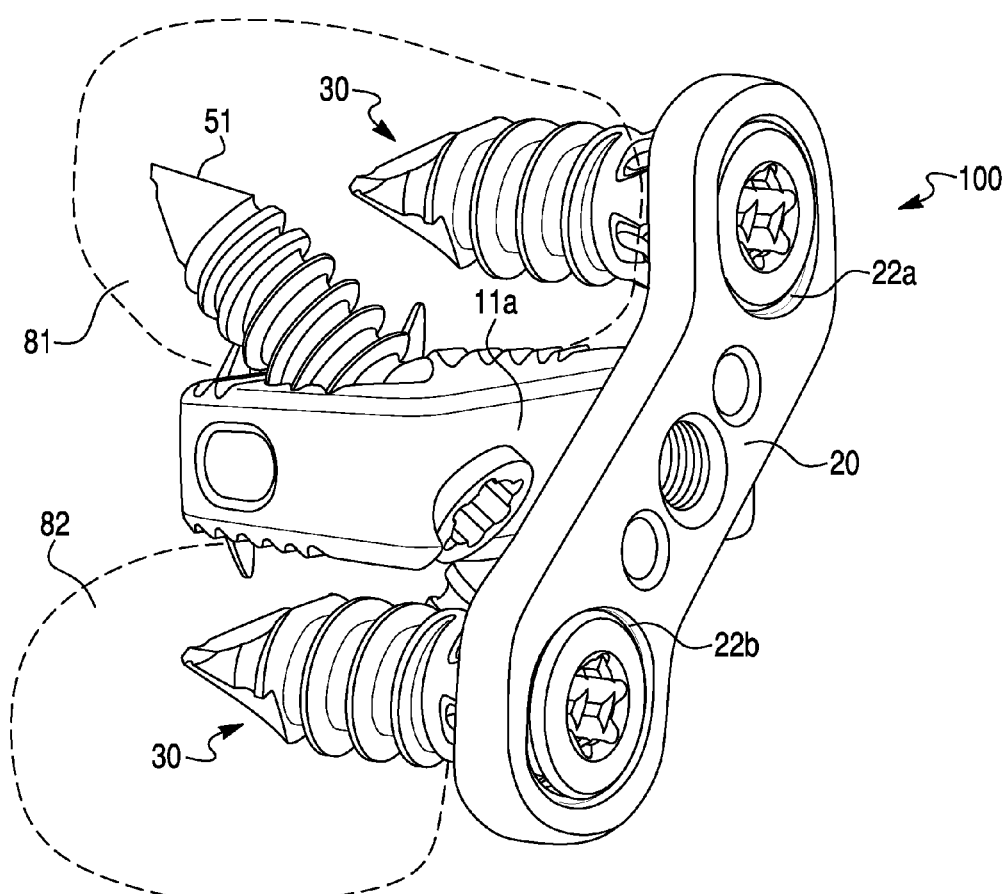
FIG. 7 is a perspective anterior view of an interbody device and system including the mounting system of FIG. 3.

FIG. 7 is a perspective anterior view of one exemplary embodiment of an interbody device/system 100 made in accordance with principles of the disclosed subject matter. The interbody device/system 100 can include a plate 20 and a pair of fasteners 30 as described above, as well as a cage 10. The cage 10 and the plate 20 can be locked into position with respect to each other and molded, machined, printed, or otherwise formed as separate structures. The cage 10 can be configured as a generally cuboid structure suitable for placement between adjacent vertebrae 81, 82. In one embodiment, the cage 10 is intended to be used in the cervical region (C3 through C7) of the spine. The cage 10 can also be shaped so as to provide restoration of disc height when placed between the vertebrae 81, 82 and to generally mimic the spacing and structure of an intervertebral disk in this region. The plate 20 can be provided for attachment to an anterior surface 11a of the cage 10. In the locked position shown in FIG. 7, the first aperture 22a and the second aperture 22b house a bone attachment structure configured as a fastener 30 described above for connecting the plate 20 to each of the vertebrae 81, 82. Thus, the interbody device/system 100 can include four separate attachment structures for attachment to the vertebrae 81, 82 at four separate locations, e.g., to the inferior surface and anterior surface of vertebra 81 and to the superior surface and anterior surface of vertebra 82. The cage 10 and plate 20 can be configured for use in many different medical and surgical procedures, including to create opportunities for spinal fusion in cases of degenerative instability, post-discectomy syndrome, post-traumatic instability, and other diseases, injuries, or malformations in the spine, and particularly in the C3-C7 region.

A first pair of fasteners 51 can secure the cage 10 to the adjacent vertebrae 81, 82. For example, the fasteners 51 can be configured as a typical bone screw having a rounded or tapered head. However, different types of attachment heads could be used, and different types of attachment structures could be used, such as pins, barbs, rivets, trocars, cements, and other adhesive or attachment structures. The first pair of fasteners 51 can extend through apertures formed in the cage 10.

A second pair of fasteners 30 can secure the plate 20 to the adjacent vertebrae 81, 82. The second pair of fasteners 30 can extend through the apertures 22a, 22b of the plate 20. The plate 20 and/or the second pair of fasteners 30 can be configured as described above with respect to FIGS. 1-6. Thus, the second pair of fasteners 30 and the cage 20 can facilitate proper positioning of the cage 10 and can discourage migration of the cage 10 after implantation in a patient.

FIG. 8 depicts the interbody device/system 100 of FIG. 7 and includes specific detail with respect to an exemplary attachment structure that can be used to attach the cage 10 to the plate 20. For example, at least one flange 125a can be located at a distal end of a shaft 125s (see FIG. 4). The flange 125a is shown as being shaped as a substantially semicircular lobe. However, the flange 125a can take on many different shapes that can perform the appropriate keyway function depending on application, design choice, or other criteria.

FIG. 4 shows the angular relationship between the extension direction of the flanges 125a and the longitudinal axis LA of plate 20. It should be noted that the plate 20 itself can also be arched such that the longitudinal axis LA curves inward towards the key 125 at the top and bottom of the plate 20 in order to facilitate mating with a bone or tissue surface. The shaft 125s of the key 125 can also be split such that the flanges 125a can move relative to each other while being biased to return to an original position under a predetermined biasing force.

In FIG. 8, the cage 10 includes an exemplary keyway 15 which is shaped as a substantially (i.e., totally or almost totally) circular cylindrical aperture extending from the exterior anterior surface of the cage 10 to an interior portion of the cage 10. The keyway 15 can be located in a recess, such as square recess 16, located in the anterior face of the cage 10. The recess 16 can be configured to mate with a locking structure of an insertion tool and can also be configured to mate with a structure, such as boss 125g, in the plate 20 to positively position the plate 20 relative to the cage 10 when they are joined together.

The keyway 15 can include at least one key flange opening 115a extending from a periphery of the cylindrical aperture. The key flange opening 115a can run along an interior face of the keyway 15 and parallel with the longitudinal axis of the cylindrical aperture. The cross-section shape of the key flange opening 115a as viewed from a longitudinal/central/symmetrical axis of the keyway 15 (as viewed in FIG. 8) can be shaped and dimensioned to match the shape and dimensions of one of the key flanges 125a. Thus, the keyway 15 and key flange opening 115a will allow the key 125 and key flanges 125a to pass therethrough. In addition, if keyway 15 and key flange opening 115a are constructed with appropriate tolerances with respect to the key flange 125a and key 125, the keyway 15 can provide some amount of support and guidance for the key 125 as it passes along the keyway 15.

Similar to the description above related to the many different shapes and orientations possible for constructing the flange portion 125a, the key flange opening(s) 115a can also be formed in many different shapes, sizes, dimensions and orientations.

As shown in FIGS. 4, 5 and 8, the flange portions 125a are oriented such that they extend at an angle relative to a longitudinal axis LA of the plate 20 when viewed from a front of the plate 20. The key flange openings 115a, as shown in FIG. 8, can be oriented such that they extend in a direction substantially parallel with a central axis CA of the cage aperture 12 (i.e., substantially vertically).

Installation indents 123a, 123b can be formed in a front anterior surface of the plate 20 on either side of the keyway 125 such that an installation tool can be threaded into an internal surface of keyway 125 while projections on the installation tool lock into indents 123a, 123b. Thus, relative rotation between the plate 20 and insertion tool can be prevented during installation due to the projections on the installation tool locking into indents 123a, 123b. The indents 123a, 123b can be formed in various manners, such as slots, apertures extending entirely through plate 20, projection structures that mate with the projections on the installation tool, etc.

As described above, the pair of fasteners 30 and the plate 20 can be configured to facilitate proper positioning of the cage 10 and to discourage migration of the cage 10 after implantation in a patient.

FIG. 9 is a partial perspective view of an exemplary plate 20, fastener 30, and removal tool 60 made in accordance with principles of the disclosed subject matter. In this example, the removal tool includes an engagement structure 62 at its distal most end (e.g., a left hand threaded portion) that mates with a tool engagement structure 42 (for example, mating left hand threaded portion) located in the head 36 of fastener 30. Once the engagement structure 62 is locked to fastener 30 (e.g., when the threads reach the bottom of the threaded portion in fastener 30), the removal tool 60 is then locked to the fastener 30, and (further) counterclockwise or left hand rotation will cause the threads on the shaft 38 of the fastener 30 to back out of the structure to which the fastener 30 is connected (e.g., bone, tissue or vertebra). As the fastener 30 backs out of the bone or vertebra or other tissue, the chamfer 26a on the plate 20 will cause the petals 48 of the collar 40 to restrict until the collar 40 has an outermost circumference that can pass through the aperture 22a in the plate 20. Thus, the fastener 30 can be detached from both the connective structure (e.g., bone or vertebra or other tissue) and from the plate 20. Flats 44f can be provided about an outer circumference of the lip 44 of the head 36 of the fastener. These flats 44f can also be used to remove the fastener 30 from the connective structure and/or plate 20. For example, if six flats 44f are spaced equidistantly about the lip 44 of the fastener 30, a hex-head socket driver or ratchet could be used to either drive or remove the fastener 30.

FIG. 10 is a partial lateral view of the fastener 30 and partial cross-section view of the plate 20 of FIG. 9, while FIG. 11 is a partial perspective view of the fastener 30 of FIG. 9. In these views, the flats 44f can be clearly viewed. In this embodiment, the transition between the head 36 and collar 40 of the fastener 30 includes an arrowhead shape flat or structure 36n. The outer radial most surface of the collar 40 is slightly larger than the inner circumference of aperture 22a of the plate 20. Thus, when the fastener 30 is located in this position, the proximal most surface of the collar 40 (in this example, chamfered surface 46) can be in contact with the inner chamfer 26a of the aperture 22a. In addition, lip 44 of head 36 can reside in and contact chamfer 24a on the top or proximal side of plate 20. Thus, the lip 44 and collar 40 act to sandwich the plate 20 therebetween. The force imparted by both the lip 44 and collar 40 onto the plate 20 tend to keep the plate 20 in place with respect to the fastener 30, and prevents shifting of the plate 20 during use. In particular, the plurality of petals 48 that form the collar 40 can be configured such that they impart a spring force against the chamfer 26a after installation. The root 50 of each petal 48 can be slightly thinner than a proximal most portion (located at chamfer 46) and each petal 48 can be cantilevered away from the main body of the fastener 30 and can move slightly inward and outward toward and away from a longitudinal axis of the fastener 30. Thus, the chamfered surface 26a of the plate 20 can cause the chamfered tip 46 of each petal to move slightly inward towards the longitudinal axis of the fastener. The spring force of the petals 48 (which desire to move back to their original position after being moved inward by the aperture 22a and chamfered surface 26a during installation) can cause the lip 44 of the fastener 30 to lock onto chamfer 24a located in the top portion of the aperture 22a of the plate 20.

When a user desires to remove the fastener 30 from the plate 20, the chamfered surface 26a will also assist in guiding the proximal most portion of the petals 48 further inward towards the longitudinal axis of the fastener 30 until the outermost radius of the collar 40 is narrow enough to fit back through aperture 22a in the plate 20. This removal function can be accomplished by inserting a removal tool 60 (see, for example, FIG. 9) into removal structure 42 located in a top end 32 of the fastener 30, and applying a removal force that causes the petals 48 to follow chamfer 26a and constrict such that the outermost circumference of the collar 40 is able to then fit through and be removed from the aperture 22a in the plate 20.

Figure 12:
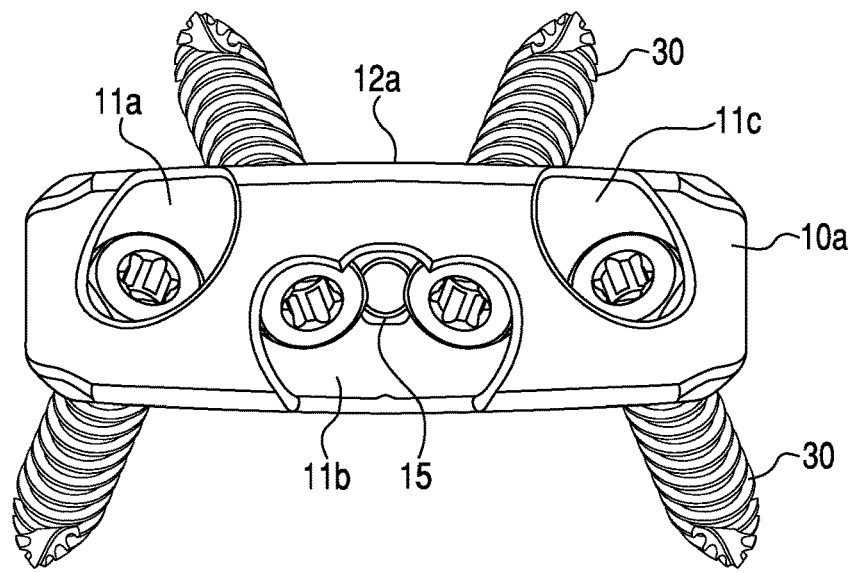
FIG. 12 is a top/superior view of another embodiment of a mounting system made in accordance with principles of the disclosed subject matter.

FIG. 12 depicts another embodiment of the disclosed subject matter in which the interbody system consists of or includes a plurality of fasteners 30 and a cage 10a. In particular, no plate 20 is required in the embodiment depicted in FIG. 12 in order to implant the cage 10a. Fasteners 30 are used to directly connect the cage 10a to vertebrae of a patient. The fasteners 30 can be configured in a similar or identical manner as compared to the fastener 30 described with respect to earlier embodiments of the disclosed subject matter. A cage 10a can include a left cage aperture 11a, a right cage aperture 11c, and a central cage aperture 11b. In this embodiment, fasteners 30 extend from both the inferior surface and superior surface of the cage 10a such that the fasteners 30 can be connected to adjacent vertebrae of a patient. A threaded aperture 15 can be located within central cage aperture 11b to allow an insertion tool to hold the cage 10a for placement between (or removal from) adjacent vertebrae.

Figure 13:
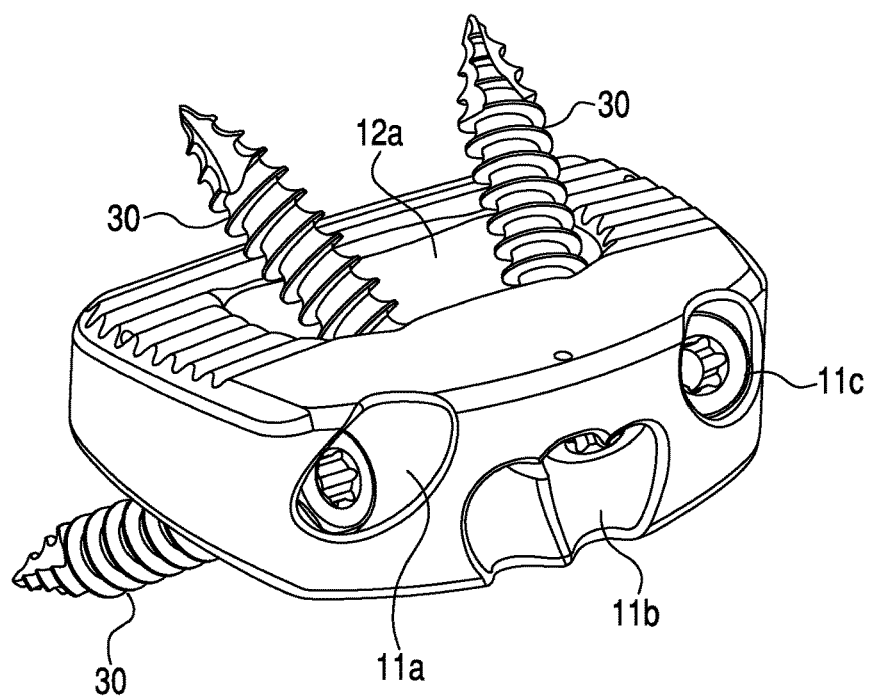
FIG. 13 is a perspective view of the mounting system of FIG. 12.

As shown in FIG. 13, two fasteners 30 can be located in the central cage aperture 11b and inserted through the anterior surface of the cage 10a to two separate openings in an inner surface of a central opening 12a in the cage 10a. The central cage aperture 11b can divide into two separate cage apertures inside the cage 10a such that two fasteners 30 can be inserted into the central cage aperture 11b and then separately extend along different and separate apertures that extend to the inner peripheral surface of the central opening 12a. When in a final implanted position, the two fasteners 30 located in the central cage aperture 11b extend from the superior surface of the cage 10a such that they can attach to a vertebra located above the cage 10a. Two additional fasteners 30 can be located in each of the left cage aperture 11a and right cage aperture 11c and, when in the final implanted position, can extend from an inferior surface of the cage 10a (opposed to the superior surface). However, the direction of each of the fasteners 30 can be changed depending on the particular application or preference. For example, the fasteners 30 that extend through left and right cage apertures 11a, 11c, respectively, can both be directed upward and away from the superior surface of the cage 10a, or each can be alternatively directed in opposing directions (one extending from the superior surface and one extending from the inferior surface). Likewise, the fasteners 30 located in the central cage aperture 11b can both be directed downward away from the inferior surface of the cage 10a, or can be alternatively directed in opposing directions (one extending from the superior surface and one extending from the inferior surface).

Figure 14:
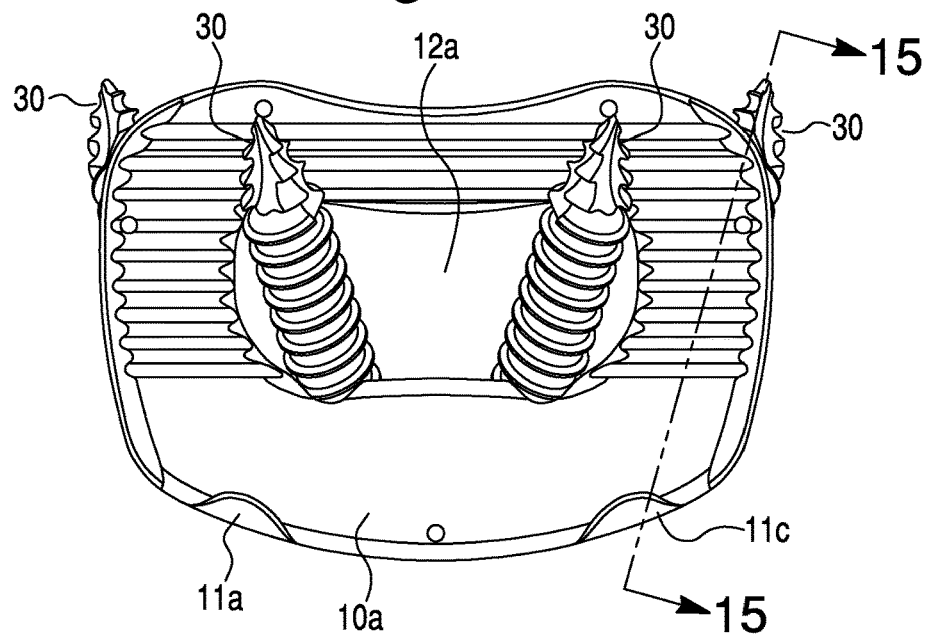
FIG. 14 is a top/superior view of the mounting system of FIG. 12.

FIG. 14 is a superior view of the cage 10a showing fasteners 30 extending from the central opening 12a of the cage 10a. In this view, the central cage aperture 11b is hidden, and the central opening 12a is configured as a kidney shaped opening that allows each of the fasteners 30 to extend from opposed lateral sides of the central opening 12a and over a portion of the superior surface of the cage 10a.

Figure 15:
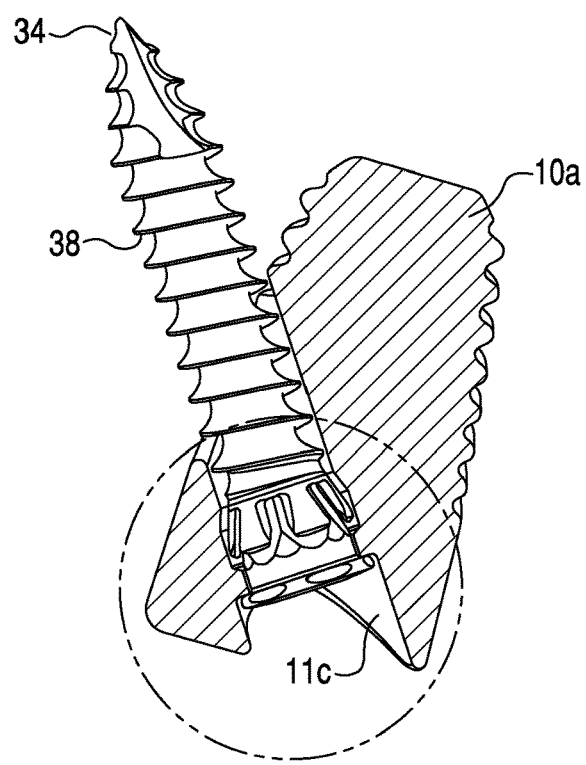
FIG. 15 is a cross-section view taken along line 15-15 of FIG. 14.
Figure 16:
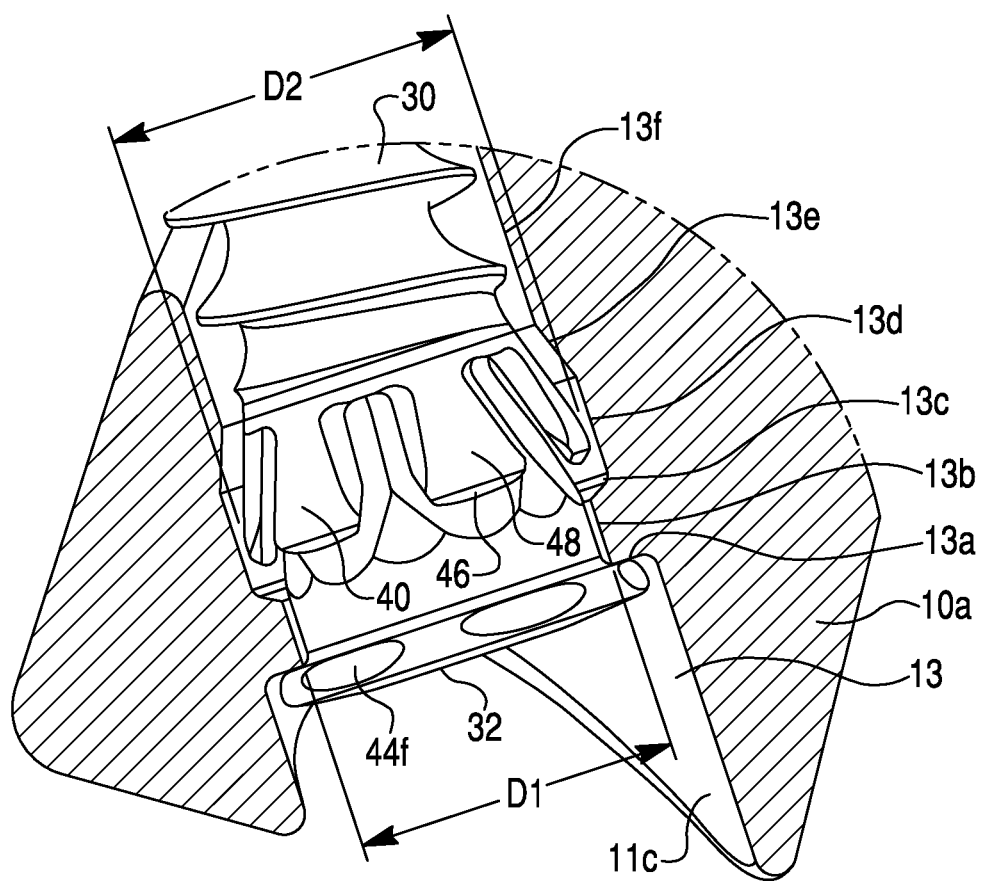
FIG. 16 is a close up view of the section shown in dashed line in FIG. 15.

FIGS. 15 and 16 depict a cross-section of the cage 10a taken along line 15-15 of FIG. 14 along with a fastener 30 shown in its final implanted position within the cage 10a. A lock structure can be defined by portions 13a-f of the inner surface 13 of the aperture 11c such that the fastener 30 can be locked in position with respect to the cage 10a when in the implanted state. In addition, the lock structure can be configured to permit detachment of the fastener 30 from the cage 10a upon particular actions/forces acting upon the fastener 30. Although only aperture 11c is shown, it should be appreciated that each of the apertures 11a, 11b, and 11c (as well as additional/other cage apertures) can include a similar lock structure.

The fastener 30 can include a lip having flats 44f spaced about the periphery of the lip located at a proximal most first end 32 of the fastener 30. A tubular or cylindrical shaft exists along the longitudinal axis of the fastener 30 between the lip at first end 32 and the collar 40. The collar 40 can include a plurality of petals 48 that are cantilevered from the shaft of the fastener 30 to provide a relatively resilient or elastic collar 40 that can change in outer peripheral diameter when exposed to a radially inward directed force thereabout.

The aperture 11c in cage 10a can include an inner surface 13 in which the fastener 30 resides when in the final implanted position. The lock structure located in the inner surface 13 of the cage 10a can be configured as an internal ring that extends from the inner surface 13 of the cage 10a. The ring can be an integral portion of the inner surface 13 or can be a separate structure that is connected to the inner surface 13 in cage 10a. In this embodiment, the lock structure includes an inwardly extending wall portion 13a that extends substantially perpendicular to a longitudinal axis of both the fastener 30 and the aperture 11c. An immediately adjacent wall portion 13b then extends distally into the aperture 11c substantially parallel with the longitudinal axes of the fastener 30 and aperture 11c. A lock surface 13c then extends from the surface 13b at an acute angle with respect to the longitudinal axes of the fastener 30 and aperture 11c and with respect to the surface 13b. In addition, surface 13c can be radiused or chamfered to facilitate mating and working cooperation with the top chamfered edge 46 of the collar 40 of fastener 30, when implanted. More specifically, the top chamfered edge 46 can ride up the angled surface 13c of the inner wall 13 to cause the petals 48 to flex inward and allow the fastener 30 to be removed from the aperture 11c, if/when desired. The inner surface 13 can then include a surface 13d that extends distally from the surface 13c in a direction substantially parallel with the longitudinal axes of the fastener 30 and aperture 11c (and surface 13b). This surface 13d is located adjacent and forms a housing for the petals 48 when the fastener 30 is in the final implanted position within the cage 10a. Surface 13e can form an acute angle with respect to surface 13d and can be configured to narrow the aperture 11c from a position adjacent the petals 48 to a final surface 13f that extends along the threads of the fastener 30 to an exit of the aperture 11c located on the inferior surface of the cage 10a.

Thus, in a final implanted position, surface 13a of inner surface may contact the lip of first end 32 of the fastener 30 to prevent further insertion of the fastener 30 into aperture 11c. By contrast, surface 13c may contact the top chamfered edge 46 of each of the petals 48 to prevent the fastener 30 from backing out of the aperture 11c. The innermost diameter D1 of aperture 11c is located at surface 13b and is slightly smaller than the outermost diameter D2 of the petals 48 of the fastener 30. Surface 13b, 13e, and 13f can act to keep the fastener 30 centered and aligned in the aperture 11c and positioned correctly with respect to the cage 10a. Thus, the surfaces 13a-13f cooperatively act to maintain the fastener 30 locked and positioned with respect to the cage 10a. In addition, the particular shape and configuration of the surfaces 13a-f allow for removal of the fastener 30 from the cage 10a should that action be necessary or desired.

In operation, the cage 10a can be located at a position between adjacent vertebrae and, once in position, fasteners 30 can be installed into cage apertures 11a, b, c. For example, fastener 30 can be inserted or rotated into aperture 11c either prior to, during, or consecutive to insertion of the fastener 30 into a vertebra of the patient. During insertion, the collar 40 of the fastener 30 will eventually come into contact with surface 13a/13b of the aperture 11c. This contact will cause each of the petals 48 of the collar 40 to flex inwardly towards the longitudinal axis of the fastener 30. This flexation of the petals 48 will allow the fastener 30 to continue in its travel direction towards the distal end of the aperture 11c and towards the inferior surface of the cage 10a. Once the petals 48 pass beyond surface 13b, they will be permitted to spring or flex back to their original shape. Once the petals 48 move beyond surface 13b, the fastener 30 is considered to be locked relative to the cage 10a and in the final implanted position. At this position, the surfaces 13c, 13d, 13e act as a housing for the petals 48 of collar 40. In particular, the surface 13c can substantially mate with the top chamfered edges 46 of each of the petals 48 to prevent the fastener 30 from backing out of the aperture 11c after implantation.

The shape of surface 13c and top chamfered edges 46 can also be configured such that, if/when desired, the fastener 30 can be removed from the cage 10a and vertebra. Specifically, surface 13c can be shaped as a ramp that allows petals 48 to ride up the ramp causing the outermost peripheral diameter of the collar 40 to restrict when a predetermined removal force is applied to the fastener 30. For example, a removal tool can be inserted in the proximal end of the fastener 30 and a counterclockwise torque can be applied to the fastener 30 to cause the fastener 30 to back out of a vertebra to cause the petals 48 to ride up surface 13c. Once the outermost diameter of the collar is then restricted to a size that can pass along surface 13b, the fastener 30 can be totally removed from the aperture 11c.

While certain embodiments of the invention are described above, it should be understood that the invention can be embodied and configured in many different ways without departing from the spirit and scope of the invention. For example, the various fastener structures need not include screw threads, and can instead be configured as rivets, pins, nails, locking structures, magnets, and other fastener structures. In addition, the collar 40 can be configured in various other shapes and configurations. In particular, the collar 40 can be a mesh or wire configuration, can include more or less petals 48, can be a complex structure with parts that move relative to each other to allow the collar 40 to expand or contract (e.g., dilate), and can include petals 48 having the same shape with respect to each other or different shapes with respect to each other. The collar 40 can also be made from a material that is different from the shaft 38 of the fastener 30 such that the spring force exerted by the collar 40 onto plate 20 can be controlled or varied. In addition, shape memory alloy(s) can be used for the entire collar 40 or portions of the collar 40, or for the fastener 30 itself. For example, the collar can include a shape memory allow that allows the collar 40 to expand or contract to provide a larger or smaller spring force after the fastener 30 is implanted. Various coatings or surface treatments can also be applied to the fastener 30 or other components of the system, such as plate 20 and cage 10. For example, ceramic coatings, bone morphogenetic coatings, osteoinductive coatings, and roughened surfaces could all be used to encourage bone or tissue ingrowth into the system 100 or fastener 30. Any of the components of the system 100 or the fastener 30 itself can include electrically conductive coatings or materials that would allow for conduction of electrical stimulation to attached tissue.

With respect to the cage 10a that includes lock structure(s) for use with fasteners 30, it is not necessary to include a lock structure in each and every one of the apertures 11a, 11b, and 11c. Only certain ones or all of the apertures can include lock structures. In addition, the lock structures can be configured differently in each of the apertures such that greater or lesser force is required for insertion and/or removal of the fasteners 30 at different locations of the cage 10a. The number and location of cage apertures can also change depending on a particular application or preference. For example, the cage 10a can include two apertures that extend from an anterior surface to a superior surface, two apertures that extend from an anterior surface to an inferior surface, and two apertures that extend from an anterior surface to lateral surfaces. In addition, the angle formed between each of the fasteners and the surfaces of the cage 10a can vary and still be within the scope of the disclosed subject matter. Likewise, the apertures can extend through lateral surfaces as well as (or alternative to) the apertures that extend from the superior and inferior surfaces of cage 10a.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A fastener having a proximal end, a distal end, and a longitudinal axis extending from the proximal end to the distal end, the fastener comprising:
   a head disposed at the proximal end of the fastener;
   a shaft connected to the head and extending to the distal end of the fastener;
   at least one of the head and the shaft including a plurality of flat surfaces;
   a collar extending about the longitudinal axis and having a proximal-most surface spaced in a longitudinal axis direction away from a proximal-most surface of the fastener, the collar including:
      a plurality of petals spaced about the longitudinal axis, each of the plurality of petals including a flat surface facing a respective one of the plurality of flat surfaces of the at least one of the head and the shaft,
   wherein the head includes a lip at a proximal most surface and a cylinder portion of the head extends downward away from the lip of the fastener and toward the distal end of the fastener along the longitudinal axis to a position directly opposing a proximal most portion of the plurality of petals, the cylinder portion of the head having a uniform outer diameter relative to the longitudinal axis, and a flat portion of the head extends downward away from a distal-most portion of the cylinder portion at a transverse angle relative to the outer diameter of the cylinder portion and adjacent to the petals.

2. The fastener according to claim 1, wherein:
   the collar further includes a top edge spaced apart from the at least one of the head and the shaft;
   a first plane containing the proximal end of the fastener is spaced from a second plane containing the top edge of the collar; and
   the first plane and second plane are substantially perpendicular to the longitudinal axis.

3. The fastener according to claim 1, wherein the collar, the shaft, and the head are integrally formed as a homogenous unit.

4. The fastener according to claim 1, wherein each of the plurality of petals is cantilevered to the shaft.

5. The fastener according to claim 1, wherein each of the plurality of petals is separated from an adjacent one of the plurality of petals by a predetermined distance.

6. The fastener according to claim 1, wherein each of the plurality of petals has a polygonal shape that includes at least one axis of symmetry.

7. The fastener according to claim 1, wherein the flat surface of each of the plurality of petals is substantially parallel with an outer surface of each of the petals.

8. The fastener according to claim 1, wherein each of the plurality of petals has a polygonal shape with chamfered edges.

9. The fastener according to claim 1, wherein each of the plurality of petals includes a root connected to the shaft and a free end extending toward the head, the free end has a cross-sectional thickness that is less than a cross-sectional thickness measured at the root.

10. The fastener according to claim 1, wherein the plurality of petals includes six petals evenly distributed about the longitudinal axis.

11. The fastener according to claim 1, wherein the head includes a tool engagement structure extending from the proximal end of the fastener and toward the distal end of the fastener.

12. The fastener according to claim 1, wherein a portion of the fastener surrounded by the collar has a hexagonal shape as viewed in a cross-sectional plane perpendicular to the longitudinal axis.

13. A mounting system comprising:
   the fastener according to claim 1; and
   a plate including at least one aperture and a plate chamfer extending away from the aperture, the aperture is configured to receive the fastener if the fastener is driven into a mounting structure, the plate chamfer is configured to displace each of the plurality of petals toward the longitudinal axis if the fastener is driven out of the mounting structure.

14. The mounting system according to claim 13, wherein:
   the lip is a circumferential lip that includes a first diameter; and
   the aperture includes a second diameter that is less than the first diameter.

15. A mounting system comprising:
   the fastener according to claim 1;
   a cage including a superior surface and an opposed inferior surface, and at least one cage aperture defined by an internal wall and configured to permit the fastener, when located in the at least one cage aperture, to extend from at least one of the superior surface and the inferior surface for connection to a vertebra, the cage including a lock structure extending from the internal wall of the at least one cage aperture such that the lock structure cooperates with the collar of the fastener to retain the fastener at a predetermined location with respect to the cage.

16. A fastener having a first end, a second end, and a longitudinal axis extending from the first end to the second end, the fastener comprising:
- a head disposed at the first end of the fastener;
- a shaft connected to the head and extending to the second end of the fastener;
- at least one of the head and the shaft including a plurality of flat surfaces;
- a collar extending about the longitudinal axis and spaced in a longitudinal axis direction from the first end of the fastener, the collar including:
  - a plurality of petals spaced about the longitudinal axis, each of the plurality of petals includes a root and a free end, the root is connected to the at least one of the head and the shaft, and the free end is spaced from the at least one of the head and the shaft such that an interior slot space is created between the free end of each of the petals and at the least one of the head and the shaft, wherein the free end is configured to flex into the slot space if force is applied the free end in a direction towards the longitudinal axis of the fastener,
- wherein the head includes a lip at a proximal most surface and a cylinder portion of the head extends downward away from the lip of the fastener along the longitudinal axis to a position directly opposing a proximal most portion of the plurality of petals, the cylinder portion of the head having a uniform outer diameter relative to the longitudinal axis, and a flat portion of the head extends downward away from a distal-most portion of the cylinder portion at a transverse angle relative to the outer diameter of the cylinder portion and adjacent to the petals.

17. The fastener of claim 16, wherein a radius extending perpendicularly from the longitudinal axis of the fastener intersects at least one of the head and the shaft, the slot space, and at least one of the plurality of petals along a substantial portion of a length of the at least one of the plurality of petals.

18. A mounting system comprising:
the fastener according to claim 16; and
a plate including at least one aperture and a plate chamfer extending away from the aperture, the aperture is configured to receive the fastener if the fastener is driven into a mounting structure, the plate chamfer is configured to displace each of the plurality of petals toward the longitudinal axis if the fastener is driven out of the mounting structure.

19. A method of attaching a component to a mounting structure comprising:
providing the fastener according to claim 16;
providing a plate including at least one aperture that is smaller than an outer diameter of the collar;
driving the fastener into the mounting structure and through the aperture to deflect the plurality of petals toward the at least one of the head and the shaft until the plurality of petals pass through the aperture and re-expand.

20. A mounting system comprising:
the fastener according to claim 16;
a cage including a superior surface and an opposed inferior surface, and at least one cage aperture defined by an internal wall and configured to permit the fastener, when located in the at least one cage aperture, to extend from at least one of the superior surface and the inferior surface for connection to a vertebra, the cage including a lock structure extending from the internal wall of the at least one cage aperture such that the lock structure cooperates with the collar of the fastener to retain the fastener at a predetermined location with respect to the cage.

\* \* \* \* \*